(12) United States Patent
Van Eelen

(10) Patent No.: US 7,270,829 B2
(45) Date of Patent: Sep. 18, 2007

(54) INDUSTRIAL PRODUCTION OF MEAT USING CELL CULTURE METHODS

(76) Inventor: Willem Frederik Van Eelen, Sumatrakade 99, Amsterdam (NL) NL-1019 PJ ( * ) Notice: Subject to any disclaimer, the term of this patent is extended or adjusted under 35 U.S.C. 154(b) by 274 days.

(21) Appl. No.: 11/124,372

(22) Filed: May 9, 2005

(65) Prior Publication Data

US 2006/0029922 A1    Feb. 9, 2006

Related U.S. Application Data

(63) Continuation of application No. 09/581,912, filed as application No. PCT/NL98/00721 on Dec. 18, 1998, now abandoned.

(30) Foreign Application Priority Data

Dec. 18, 1997   (WO) ..................... PCT/NL97/00710

(51) Int. Cl.
*A61K 47/00* (2006.01)
*A23L 1/31* (2006.01)
*C12N 11/14* (2006.01)
*C12N 11/08* (2006.01)
*C12N 5/06* (2006.01)

(52) U.S. Cl. .................. 424/439; 424/93.7; 426/7; 426/802; 435/176; 435/178; 435/180; 435/395

(58) Field of Classification Search ................ None
See application file for complete search history.

(56) References Cited

U.S. PATENT DOCUMENTS

| 5,624,840 A | 4/1997 | Naughton et al. |
| 6,835,390 B1 | 12/2004 | Vein |
| 2005/0084958 A1 | 4/2005 | Vein |

FOREIGN PATENT DOCUMENTS

| GB | 1 433 841 | 4/1976 |
| JP | 2002-191326 | 7/2002 |
| WO | 94/08598 | 4/1994 |
| WO | 94/28738 | 12/1994 |
| WO | 96/40889 | 12/1996 |

OTHER PUBLICATIONS

Chromiak et al., In Vitro Cellular & Developmental Biology Animal 34 (9) : 694-703 (Oct. 1998).
Yamamoto et al., Retardation of Phenotypic Transition of Rabbit Arterial Smooth Muscle Cells in Three-Dimensional Primar Culture, Experimental Cell Research 225(1): 12-21(1996).
Molnar et al., "Skeletal Muscle Satellite Cells Cultured in Simulated Microgravity", In Vitro Cellular and Developmental Biology Animal 33(5): 386-391 (May 1997).

*Primary Examiner*—Sandra E. Saucier
(74) *Attorney, Agent, or Firm*—Young & Thompson

(57) ABSTRACT

A meat product containing in vitro produced animal cells in a three dimensional form and a method for producing the meat product.

5 Claims, No Drawings

INDUSTRIAL PRODUCTION OF MEAT USING CELL CULTURE METHODS

This application is a continuation of application Ser. No. 09/581,912 filed on Jan. 12, 2001, which is the 35 USC 371 national stage of PCT/NL98/00721 filed on Dec. 18, 1998, which claimed priority to international application PCT/NL97/00710 filed on Dec. 18, 1997.

SUMMARY OF THE INVENTION

The subject invention is directed at the production of a meat product. The product itself also falls within the scope of the invention.

BACKGROUND OF THE INVENTION

The current world population is exceedingly large and still growing. In order for the population to be fed sufficiently more and more land is required for food produce. The natural sources are insufficient to fulfil the demand. This has led to famine in some parts of the world. In other parts of the world the problem is being addressed by large scale production of animals often under atrocious inhumane conditions.

This large scale production is not only causing unnecessary great suffering to animals. It is increasing the number of diseases and the consequences thereof for both animals and humans. Large scale slaughtering is currently required to fulfil the current food requirements and as a consequence of large scale disease outbreaks. We can take for example the recent large scale occurrence of porcine pestivirus and mad cows disease. These diseases also result in loss of the meat for human consumption thus completely denying the purpose for which the animals were being bred in the first place.

In addition the large scale production is reducing the flavour of the finished product. A preference exists among those that can afford it for non battery laid eggs and non battery produced meat. Not only is it a matter of taste but also a healthier choice thereby avoiding consumption of various feed additives such as growth hormones.

Another problem associated with mass animal production is the environmental problem caused by the enormous amounts of excrement the animals produce and which the environment subsequently has to deal with. Also the large amount of land currently required for animal production or the production of feed for the animals which cannot be used for alternative purposes such as growth of other crop, housing, recreation, wild nature and forests.

A solution has been sought for the above-mentioned problems and is described in detail below.

DETAILED DESCRIPTION OF THE INVENTION

The subject invention is directed at solving the above mentioned problems by providing a novel production process for meat. The invention also covers the food product itself. The novel process does not require the large scale inhumane production of animals (bio-industry) and in fact does not require the loss of any animal life or animal suffering. The process does however render a product that is healthy and free of growth hormones at levels exceeding physiological levels. The product can replace current meat products.

The subject invention is directed at a process for production of a meat product said process comprising the culturing in vitro of animal cells in medium free of hazardous substances for humans on an industrial scale thereby providing three dimensional animal tissue suited for human consumption, said cells being selected from muscle cells, somite cells or stem cells.

Industrial scale means on a scale other than laboratory scale. Thus the cultivation containers used for cell growth will be larger than 5 litres, and can even be larger than 5000 litres. Preferably this means on a scale for production similar to that applied for example in the production of yeast cells in the food sector or in the penicillin production field about which numerous publications are available to the person skilled in the art.

To date the three dimensional production of muscle cells, in vitro had not been carried out. Three dimensional means in a manner resulting in a composition comprising multiple cells forming one structure in all three dimensions. To date explant cultures whereby tissue was extracted in vivo and placed on a petri dish and cultivated resulted in the growth of monolayers of muscle cells. This process was only carried out on laboratory scale in order to assist in the medical world either in research directed at ascertaining growth related characteristics or directed at medical wound treatment. The explant culture technique has never been used or suggested for application in food production. In fact this technique is not suited for food production as the process mainly is directed at keeping the extracted tissue alive rather than generating large amounts of new muscle cells as a tissue. A description of the explant technique can be found for example in Wounds 1991;3 (3):102-110 an article coauthored by one of the subject inventors (The authors of the cited article are C. Le Poole, P. K. Das, S. R. Krieg, J. R. Mekkes and W. Westerhof). In medical literature monolayer cultures of striated muscle cells were used to study metabolism and kinetics, in physiological and pathophysiological context. In the literature one can also find descriptions of in vivo culture of muscle tissue in the context of wound healing or partial organ replacement, however, such a method has not been taught or suggested for food production and is in fact not suited therefore. It would not solve the problems already addressed above for conventional meat production.

Contrary to the existing belief that the in vitro culture of three dimensional muscle tissue was impossible due to the inhibitory action exerted by the muscle cells themselves upon contact with other muscle cells the subject inventors have found a process that actually provides three dimensional muscle tissue. The same is valid for stem cells and somite cells. The Example provided shows in detail how this technology can be applied for these cells. We refer to a number of articles which provide detailed descriptions leading from somite cells and stem cells to differentiated cells like muscle cells, blood cells and blood vessels (Mummery et al 1990 and 1993, Slager et al 1993, van Stekelenburg-Hamers 1995 and thesis 1994). The content of these cited documents is incorporated by refernce. We also point out that the method for producing meat can also comprise culture of a number of other cell types such as blood in addition to the muscle cells. The methods indicated in the cited articles are capable of upscaling to industrial scale without requiring substantial changes in methodology. Where application of antibiotics is mentioned in the examples and the cited references these can be omitted and the use of sterile conditions e.g. in a clean room can be introduced instead. The process according to the invention thus offers the possibility of meat production free of hazardous substances. Such a hazardous substance is an antibiotic e.g. penicillin. It is also intended to carry out the method according to the invention in absence of antibiotic. It is also intended to carry out the method in absence of hormones. Specifically in absence of corticosteroid hormones like dexamethaxon, cortisol and hydrocortisone. Subsequently the resulting food product is thus also free of hazardous antibiotics and hormones. Specifically the advantage is seen for the absence of steroid hormones as these are exceptionally hazardous. The process is also to be carried out in absence of hyaluronic acid derivatives. Preferably the process is also carried out in absence of bovine serum with a view to circumventing any contamination with BSE or mad cows disease causing viral material.

Alternatively the three dimensional culture is contemplated as occurring on a matrix as described in a manner analogous to that disclosed. The muscle cells to be used in such a new procedure can in turn be obtained from procedures as illustrated in the examples. The same is valid for stem cells and somite cells. The matrix can be collagen or a synthetic substrate. If the latter is non-digestible, it should be removed during work up to the edible end product. In an alternative embodiment culture can occur in suspension or by producing monolayers and subsequently compacting a number of grown monolayers to a three dimensional structure. The technical details for these embodiments can be derived from literature available to the person skilled in the art from the medical literature for monolayer cultivation of muscle cells in vitro. The process naturally needs to be upscaled to industrial scale to render it a suitable process for food production.

In a preferred embodiment the cells to be cultured are selected from somite cells which are cells in the predifferentiated stage preceding muscle cells. The somite cells can be taken from tissue in a manner known per se. The regenerative power of such cells is larger than that of already differentiated cells and as such could ensure a higher production per cell used in the original culture. Stem cells form an alternative source of cell material.

As such the invention is not merely directed at a novel production process but at a novel food product, consisting of in vitro produced animal cells in a three dimensional form i.e. comprising multiple cell layers of animal cells in three dimensions, said meat product being free of fat, bone, tendon and gristle and preferably free of growth hormones in non physiological amounts, said cells being selected from muscle cells, somite cells and stem cells. As it is free of tough products, the product is easier to consume for the ageing population.

The product retains the structure and flavour of lean meat without the ensuing animal suffering or concomitant ethical, religious, economical and environmental problems associated with regular production of meat comprising food products as detailed above in the introduction. The resulting product is thus healthier and also has better texture than standard meat. The subject product can be used to replace current animal produced meat as food or component of food products such as sausages, processed meats, soups, stews, purees, granulated protein products and regular meat cuts. The novel product according to the invention can be produced in unit sizes enabling ease of transport and storage. The product can be factory produced in a largely automated process as is common in known food processing processes requiring cell culture. The final product exiting from the factory can be packaged in situ either in fresh, precooked, dried or frozen form analogous to meat obtained from live animals without requiring a step of the removal of debris and offal. It can be discerned from other current meat produce due to the lack of fat, bone, tendon and gristle and the regular and uniform composition of the muscle cells. the required consistency for application can be achieved by denaturing the protein once it has been produced e.g. by cooking, boiling etc much in the manner analogous to treatment of the proteinaceous substance of eggs i.e. protein solidification steps.

In a preferred embodiment the novel food product according to the invention can further comprise nutritional additives such as vitamins and minerals to further enhance the nutritional value thereof. Care should be taken to keep the resulting product as natural as possible, thus additives should be used within physiological boundaries. Due to the production process of the novel product it is simple in a controlled manner to enhance the nutritional value by adding the desired added nutrient or compound to the growth medium in a form accessible to the cell.

The cells can be cultured in admixture with the muscle cells, somite cells or stem cells or be cultured separately and added in an amount according to choice to the cultured muscle cells prior to processing of the cell culture of muscle cells to the final product. The processing to the final product will be different depending on which method of cell culture is selected. The process comprises bringing the cell culture to a solid state and texture comparable with that of in vivo derived meat. The exact methodology for working up from the cell culture will be a matter of choice dependent on the destination of the final meat product and whether it is to be fresh, dried, frozen, pre or partially cooked, pickled or smoked etc. and is to be incorporated in a food product such as soup, stew, sausage, spread, puree e.g. baby food, biscuit or dried granules, tablet or powder etc. The advantage is that such further processing can easily be combined with the original process of producing the animal cell ingredient of the finished food product and does not require the traditional steps of offal removal, deboning and removal of gristle, tendon and/or fat. The cells can be derived from mammals, e.g. cow, sheep, goat, pig, deer, rabbit, hare, whale, kangeroo; birds, e.g. chicken, goose, pheasant, duck, ostrich and partridge; reptiles, e.g. frog, turtle, crocodile; fish, e.g. tuna, eel, cod, sole, shark and herring; and shellfish, e.g. oyster, crab, langoustine and shrimp. Mixtures or combinations of the above can also be made.

For initiating this industrial meat/fish vital cell culture method according to the invention per animal sort only a small number, preferably intracellular 100% pure embryo muscle or somite cells are required. These initial cells can be obtained from specially selected donor animals for this purpose. The donor animals are kept under very strict environmental conditions, i.e. in quarantine, in clean rooms and with feeding conditions etc. during a longer period under the directions of a team consisting of i.a. a biologist, a surgeon, a histologist, a veterinarian surgeon, a computer programmer, a chemist, a bacteriologist, a pharmacologist, a technical engineer and any other scientific staff. For these initial cell cultivating procedures it is not necessary that the donor animals be killed or slaughtered. These selected and supervised donor animals will be treated in an animal friendly manner and by detoxification treatment and correct feeding the current serious environmental burden on animal cells will be combatted which will improve the general degree of health, resistance and germination strength in an optimal manner. For this objective computer regulated cell quality control e.g. in combination with the aid of an electron microscope can be used. In addition, the donor animals should regularly be checked by veterinarians with serological and bacterial assays for infectious diseases such as salmonella infection, brucellosis, listereosis, leptospirosis, toxoplasmosis and Q-fever and tuberculin tests. By means of this specially regulated supervision the muscle/somite cells can continually progress with cell division for meat production outside the intact organism. In particular, the composition of the feeding medium is of large importance for this cell division for 100% pure meat/fish production. G. M. Heally and associates developed a feeding medium 858 consisting of 62 ingredients, namely 20 amino acids, 12 vitamins, 7 co-enzymes, 2 lipid sources, 5 nucleic acid products, 3 antibiotics and serum. This medium resulted in a 10-fold increase of the number of cells. Such feeding media and others can be used for the culture of the meat vital cells according to the invention. Naturally adaptations of such media can be suitably used. In addition it is important to regulate any undesired changes of pH and oxygen in a continuous manner by computer. The muscle/embryo and somite cells growth required for this 100% pure meat production according to a new unique industrial cultivation method and can be computer regulated and quality controlled to provide a 100% pure protein product. Doctor Robin Holliday of the National Institute for Medical Research in London is of the opinion that the dying of (culture) cells should be attributed to errors. Dr. Holliday carried out experiments in this regard with fungi. These fungal cell cultures which normally practically have eternal life started to age quickly when errors were introduced into the fungal cell cultures. Fungal cultures however where these errors were not introduced could live on endlessly with their vital culture cells. Current meat and fish comprise material with the same errors as introduced in the fungal cells because proteins of insufficiently checked slaughter cattle exhibit a strong increase in erroneous, less than 100% normal proteins due to their bad food and maintenance conditions. So current cattle and the meat/fish producing animals will i.a. by wrong environmental influences increasingly comprise meat or fish that is produced by the current methods with bad proteins. This will result in an increase in more bad proteins being introduced into the human metabolism i.e. result in an increased aging, a reduced immune system and increased susceptibility for breading of disease. Thus, lending credence to the adage "you are what you eat". With increasing age (after the embryo state) under influence of the current negative environmental influences, the cells of living animals will become increasingly less healthy, for example by poisoning of the tissue fluid i.e. the internal medium of muscle cells of cattle. The molecular biologist Dr. Robin Holliday clearly thus sees the cause of disease, fatigue increased aging and negativism in the cellular autoimmunization processes taking place. The findings of Dr. Holliday can be found in Nature 221, 1969, p. 1234-1238. Also Dr. L. J. Orgel of the Salk Institute in San Diego published in Proc. US Nat. Acad., set 49, 1963, p. 517 a connection between increased negative factors and increased aging with bad proteins. Theoretically it means that the number of "bad proteins" increases by mistakes in the cattle in the growing process. From these erroneous proteins a large number of erroneous proteins will be derived which will in turn mean that the total metabolism of cells will no longer function properly and the erroneous proteins will result in development of specific antibodies with all the consequences thereof to the animal and the consumer of such animal product. Recent newspaper articles also indicate that the contamination of ground and water in the environment to which cattle are exposed are also resulting in toxicological compounds having a profound effect. Prof. Dr. P. Schepens, a professor in Antwerp indicated that drinking water in the lower lying areas such as the Netherlands are contaminated with carbondisulphide which apparently causes a disease similar to aids in cattle. In a number of cows lately mysterious diseases have been found, such as dysfunctional growth, skin problems, swollen joints and equilibrium problems. The cause could be due to intensive oil and gas winning which resulted in contamination of the salt swamp lands lying approximately 50 cm to 5 m below sea level. During a number of decades upward water streams have brought oil up to the surface. According to Dr. G. Counotte, a toxicologist at the Health Service for Aminals approximately 70% of the surface water is contaminated. According to Dr. Counotte within a couple of years the cattle to the West of Utrecht in the Netherlands will need to be destroyed. Thus, it is of the utmost importance that the industrial meat/fish production according to the invention having a 100% pure protein composition is implemented as soon as possible within the near future to prevent the continued environmental burden and to enhance the current health of the population and in particular to enhance the health of future generations. The applicants of this patent are committee members of Foundation Worldwide Medical Water Oriëntation. This foundation has as objective cooperation with the United Nations and other aid organisations to enable the provision of good pure drinking water in developing countries in refugee camps and i.a. in the ghettos of large cities in South America etc. In addition, the foundation has as task enabling grounds in areas where it is too warm and where insufficient rain falls to be rendered useful for agricultural by means of a new system, in order to attain better health and more prosperity. Any revenues to be realized upon exploitation of this patent are also destined to be used to finance the above-mentioned objectives of the foundation. The chairman of the foundation, W. F. van Eelen, already had the idea of this patent application in view of the enormous importance of the exploitation of the possibilities mentioned in the patent in 1950 during his studies and followed the scientific developments for many years thereafter in order to arrive at the subject matter described in the patent application. In this respect and in view also of the current environmental problems knowing that his important idea of 47 years ago had now become technically and scientifically exploitable he already deposited the idea at the roots of the subject patent application under a secrecy agreement with the Inland Revenue Service of The Netherlands in Rijswijk for purposes of establishing date of conception at least as early as Mar. 3, 1995. Proof of this is presented as enclosure 1. The translation of the deposited text is as follows: "The industrial production with new techniques on a large scale i.a. using elements of laboratory tissue cell culture method of all 100% pure meat and fish sorts with complete maintenance of exterior, taste facets and character, thereby rendering the keeping of cattle (fish) and the slaughtering (catching) thereof, i.a. as economically too costly—superfluous. The consumer is provided with an in particular more tasty and more tender (where necessary) also cheaper 100% pure meat and fish. The computer regulated growth production also renders this meat and fish in all existing variations more healthy for human consumption, i.a. by the complete lack of hazardous additives and any negative environmental influences. (Positive consequences with regard to public health). I.a. by the availability of extensive grazing ground which is now required for cattle cultivation, agricultural possibilities are extended enormously which can be of interest i.a. for the environment and in addressing the world food shortage".

EXAMPLES

Materials Mentioned in Examples

Albumin bovine (BSA) BDH 1 g/vial. Cat. Nr. 44004

Amicon ultrafiltration cell 50 ml. Model 52. Amicon Comp. Lexington Mass. 02173.

Brown sterilizer control tubes for ovens at 160° C. Type 3. Green Spot. (Lameris, Biltstraat 449, 3572 AW Utrecht).

Chick embryo extract 20 ml 50% in Earle's Balanced Salt Solution. Flow. Cat. Nr. 28-501-46.

(Keeps ca. 6 months at −70° C.).

Collagenase 250 mg/flask. Sigma Cat. Nr. C-2139.

(Store at −20° C.).

Diaflo ultrafiltration Membranes 25 PM 10 43 mm.

Amicon Comp. Lexington Mass. 02173.

Dimethylsulphoxide (DMSO)) Analar BDH Nr. 10323 500 ml/bottle.

Dulbecco's Minimal Essential Medium (DMEM)×10 without L-glutamine 500 ml/bottle.

Gibco Cat. Nr. M 07-2501.

Ethylenediamine tetraacetic acid 100 g/bottle.

Dulbecco's Minimal Essential Medium (DMEM)×10 without L-glutamine 500 ml/bottle.

Gibco Cat. Nr. M 07-2501.

Ethylenediamine tetraacetic acid 100 g/bottle

BDH Cat. Nr. 28021-2Q.

Falcon Tissue Culture Flask. 25 cm$^2$ growth area, two position cap. 500/case. Becton-Dickinson Oxnard Cal. Cat. Nr. 3013.

Foetal Calf Serum (FCS) Gibco Cat. Nr. 629 HI 100 ml/bottle.

(Keeps ca. 6 months at −70° C.).

Fungizone 50 mg/flask. Squibb.

L-glutamine 25 g/bottle. Sigma Cat. Nr. G-3126. (Store at 4°).

Horse serum (HS) Gibco Cat. Nr. 605 HI. 100 ml/bottle.

(Keeps about 6 months at −70°).

Hydrochloric acid, crude, ca. 30% 1 l/bottle.

Millex Millipore Filter Units, disposable.

0.22 ìm: Cat. Nr. SLGS-025-OS 0.45 ìm: Cat. Nr. SLHA-025-OS

50/box.

Millipore Sterifil-D units, disposable. Cat. SGFS-047-LS

Millipore Comp., Bedford (Mass.)

Nigrosine 25 g/bottle. BDH Cat. Nr. 34058

Nylon filter gauze, mesh width 20 and 50 ìm. Minimal order 100×100 cm. Nyta Nylon Seidengaze. Schweizerische Seidengazefabrik CH-9425 Thal/Switzerland.

Parafilm M. American Can Comp. Dixie/Marathon greenwich Conn. 06830. 4 in×125 ft/roll.

Pasteur Capillary Pipettes. Short size 150 mm.

Penicillin-NA. 1.000.000 U/flask.

Petri dishes, sterile, disposable. 500/case. 60×15 mm.

Lux Scientific Corp. 1157 Tourmaline Drive Newbury Park, Calif. 91320. Cat. Nr. 5220.

Phenol red pH=6.8-8.4 (yellow-red). British Drug House Nr. 20090. 5 g/bottle.

Phosphate Buffered Saline×1 (PBS). 500 ml/bottle.

Flow Cat. Nr. 18-604-54.

Sodium Azide 25 g/bottle. Sigma S 2002 (Explosive!)

Sterilin containers 20 ml. 400/case. Printed Label. Sterilin Ltd., Teddington, Middlesex U.K., Cat. Nr. 128 B.

Streptomycin sulphate. 1 g/flask.

Tuberculin.

Trypsin 1:250 Difco 100 g. Difco lab. Detroit Cat. Nr. 0152-15

Water, bidistilled, 100 ml/bottle.

1. Dissociation of Muscle to Obtain Starting Material

This can be achieved by way of example in any number of manners, e.g.

A. Rinse a muscle biopsy a few times in PBS solution
B. Fill a sterilin container with dissociation solution up to 20 ml
C. Introduce the muscle biopsy into a sealable container with a wide neck and add 7 ml dissociation solution.
D. Put this container in a water bath and shake it at 37° C. such that the biopsy moves through the medium
E. After exactly 15 minutes pour off the liquid into 7 ml 10% FCS in DMEM
F. Add 7 ml again to the biopsy and disrupt the biopsy somewhat by pulling, however, do not divide into parts
G. Reintroduce into the bath at 37° C. for 15 minutes and repeat the same procedure twice.
H. After which add the three containers with 14 ml (7 ml dissociation solution and 7 ml 10% FCS) to each other and centrifuge at 1200 rpm for 5 minutes
I. Dissolve the pellet in 4 ml 20% FCS and in a 75 CM culture flask and give the cells 24 hours to attach
J. Rinse after 24-48 hours and replenish with 20% FCS and proceed to muscle cell culture either as trabecular matrix approach, in suspension approach or in monolayer approach.

2. Culture on Trabeculated Medium

The muscle cells that can be obtained in any of the procedures of 1 can subsequently be used in a culture of cells in trabeculated medium. The trabeculated medium will preferably having a poresize of 25-200 ìm, preferably 30-150 ìm Dry collagen sponges, for example of a thickness of 2-20 mm can be fabricated in a freeze-drying process from insoluble native collagen type I fibres of bovine origin. Subsequently the sponges can be coated with á-elastin hydrolysate from bovine ligamentum nuchae in a concentration of 3 w/w %. It is also known from the state of the art that recombinant collagen or collagen derivatives can be produced, naturally these can be used in the production process if so desired. The cell populations can be seeded into the collagen sponges at a concentration of $10^5$ viable cell/$cm_2$. This can be placed on a flat container e.g. a petri dish or in a cylindrical container into which the matrix is placed in a folded manner or it can be rolled into a three dimensional structure through which medium is percolated. The medium can be refreshed as often as necessary, e.g. one or two times a week. Such a system can be automated. There is less risk of infection and cells that are not continually being replated will have a longer replication life time with the concomitant advantages thereof. The container with myoblast containing sponges can be maintained at culture conditions allowing attachment to the matrix fibres and by incubating. The sponges in growth medium at the required temperature growth of the cells on the cell matrix can occur. Analogously other trabeculated matrix material can be used. this can be polyurethane, polylactic acid, chitine for example. The cells can either be used together with the matrix if an edible matrix is used or be removed from the matrix as part of the production process. Once confluency has been reached the culture medium must be removed, the meat product is ready to be used and does not require further processing steps as such. If thin layers are produced, a number of layers may be combined to achieve the desired product thickness. Upscaled and automated procedures analogous to the above are preferred embodiments.

3. Culture in Suspension

The muscle cells that can be obtained in any of the procedures of 1 can subsequently be used in a culture of cells in suspension. Upscaled and automated procedures are preferred embodiments.

Cells can be added to microcarriers such as Cytodex 1 and 3 beads or dorma cells. The attachment of the cells can occur by contacting cells from a monolayer culture onto the microcarriers when these are put on top of the monolayer. In a rotating system the growth of the cells on the microcarriers can take place while the microcarriers are kept in suspension. In a suitable embodiment cells and carriers can be combined in a ratio of 10:1 in 25 ml of growth medium (1 mg carriers/ml) in culture flasks. The flasks can be gassed with 5% $CO_2$ and sealed. After adjustment of the pH of the medium to 7,2 cells and carriers can be transported into 25 ml test tubes which are subsequently sealed. These test tubes can be rotated at 7 rpm on a Cel-Gro Rotator (Lab Line Instruments, Inc. IL) in a cultivation chamber at 37° C. Medium can be refreshed twice a week after settling down of cells and carriers. It is also possible to carry out the experiment in a cell culture fermenter vessel comprising 2 mg/ml; $0,8 \times 10^3$ carriers/ml of for example Cytodex 3 microcarriers and inoculating these in a ratio 9:1 in 1.2 litres of growth medium, e.g. 10% FCS. The carriers can be kept in suspension with a cell lift impeller at an agitation speed of 22-25 rpm. The temperature of 37° C. and pH of 7.2 and the dissolved oxygen, amount of 50% can automatically be controlled by the cell culture system (Celligen, New Brunswick Scientific Co., Inc., Edison, N.J.). Medium can be refreshed batchwise (0,5 l) twice a week after cells and carriers have settled. After growth the cells can be detached from the microcarriers, for example by incubation in 0.02% EDTA and 0.005% trypsin in PBS-3. Cells can subsequently be separated from the carriers by filtration over 150 ìm screen in a Cellector, tissue sieve (Bellco Glass, Inc., Vineland, N.J.). Cells in the filtrate can be harvested as cellpellets after centrifugation or used for repeated culture.

The attachment to cytodex 1, cytodex 3 and dorma cells can be seen to occur almost immediately after cells and carriers are combined. Subsequently the cells spread on the microcarriers within a couple of hours. In both the suspension in the rotating system as in the fermenter system good growth is obtained and growth to confluency or near confluency was also obtained relatively quickly. When confluency or near confluency on microcarriers is reached detachment of parts of the cell sheet from the microcarriers occurs. In the stationary system this results in reattachment to the culture flasks surface. In the rotating systems these unattached cells can be harvest at medium refreshment and can be used for replating in culture flasks or be harvested for use in the production of the food product. In the rotating test tubes almost complete confluency is reached on all the carriers resulting in a cell density a lot higher than on the culture flasks surface. The results in the fermenter system prove that enormous quantities of cells can be obtained in a very short time. In the fermenter system it also is easier to maintain large quantities of cells as opposed to culture flasks in view of being less labour intensive with less risk of contamination and requiring less space or storage than for the flasks. Depending on the cell type, the media and the growth conditions can be optimized in a manner clear to a person skilled in the art. Higher agitation speed and carrier concentrations during inoculation can for example result in a more even distribution of cells over the carriers. Extra addition of amino acid vitamins, glucose and attachment factors or medium refreshment by perfusion could also improve the results. Scaling up to a 2.5-1 vessel is expected to provide cell numbers in the order of $10^9$.

4. Culture in Monolayer 4.1. Myoblast Culture in Monolayer

Procedure:

A. Contact the myoblast culture with FCS fungizone medium.

B. Place flask into incubator without shifting the content.

C. Replace medium after 72 hours if yeast or fungus remain and use FCS fungizone for another 72 hours. Use 20% FCS for this treatment.

D. Incubate at 37° C., 5% $CO_2$ with a relative moisture of 98%. Myoblast proliferation occurs at a rate wherein doubling occurs in three to four days. Do not let the myoblast culture become confluent. At a maximum let it grow to 60 to 70% confluence then trypsinate immediately.

E. To trypsinate seed a 25 $cm^2$ Falcon flask with 50-80.000 myoblast in 4 ml FCS medium.

F. When the cells have been proliferated then preplate them in 75 CM culture flask, i.e. simply trypsinate and replace in a 75 CM flask and return to the incubator.

G. After exactly 20 minutes the container can be carefully put upstanding and the supernatant can be transferred to a clean 75 CM flask. In this treatment most of the fibroblasts which are always present in a myoblast culture will remain behind in the first flask because these fibres adhere quicker than the myoblasts. These fibroblasts can disturb differentiation and for this reason must be removed. Please note the fibroblasts will only be present in the first sample, subsequent cycles of proliferation will be already free of fibroblasts and will not require this step.

H. Upon sufficient density (approximately 70% confluent) the cells can be replenished with differentiation medium which will enable formation of myotubes, an irreversible process that takes place approximately after 6-8 days. These myotubes cannot be trypsinated and should not be replenished during the differentiation. These myotubes only remain for a few days and than collapse.

4.2. Harvesting of Monolayer Cultures

I. Preparation:
  A. Switch on laminar flow cabinet before onset of procedure
  B. Clean rear, sides, and bottom of flow cabinet with alcohol 96%
  C. Put in the cabinet:
    1. Enough weighed and labelled Eppendorf cups
    2. Beaker with ice containing:
      a. Eppendorf cups, placed there immediately before each harvest.
      b. 1 Sterilin container with 10-15 ml PBS (Flow)
    3. Bottle of 500 ml of PBS (need not be or stay sterile)
    4. Rubber "policeman"
    5. Kitchen knife
    6. 100 ìl pipette
  D. Place beside the cabinet:
    1. Yellow pipette tips (for 100 ìl pipette)
    2. Syringe with 70% alcohol and a tissue, for cleaning the policeman after each use.

II. Procedure.
  A. Take a small (25 cm²) Falcon bottle from the incubator Screw the cap on tightly.
  B. If necessary, examine it under the microscope, or take a picture of it.
  C. Using the kitchen knife, snap off the top side of the Falcon bottle.
  D. Remove PBS and any plastic bottle fragments.
  E. Remove the medium by suction, and add 3 ml of PBS from the 500 ml bottle, leaving a 10 ml pipette standing in the bottle.
  F. Remove and replace the 3 ml of PBS.
  G. Replace and remove 3 ml of PBS.
  H. Add 400 ìl of PBS (2×200 ìl, using the 200 ìl pipette from the Sterilin container.
  I. Using the rubber policeman, scrape PBS and cells into corner.
  J. With same blue tip, pipette the cell-PBS suspension into the Eppendorf cup in the beaker on ice.
  K. Put the Eppendorf cup into the freezer, immediately and upright.
  L. Discard pipette tip and remnant of the Falcon bottle.
  M. Cleanse the policeman with a tissue soaked in 70% alcohol.
  N. Replace ice in beaker if necessary.
  O. After harvesting all bottles, rapidly weigh all the Eppendorf cups, and store them in the −70° freezer.

A monolayer culture will be removed from the growth medium and a number of layers will be brought together and contacted with each other thereby forming a three dimensional food product per se or ingredient for a food product. A number of monolayers can e.g. be compacted thereby providing the finished product. In the case of a suspension the growth medium can be removed or the solid part of the cell culture comprising the cells can be removed. The exact methodology to be applied will depend on the content of the culture medium and the desirability of the final product comprising components of said growth medium other than the cultured cells.

LIST OF REFERENCES

1. Mummery, C. L., Feijen, A., Freund, E., Shen, S. (1990) Characteristics of stem cell differentiation: a comparison with two embryonal carcinoma cell lines. Cell. Diff. Dev. 30:1-18.
2. Slager, H. G., van Inzen, W. G., Freund, E., van den Eijnden-van Raaij, A. J. M. (1993) Transforming growth factor β in the early mouse embryo: implications for the regulation of muscle formation and implantation. Developmental Genetics 14:212-224.
3. Mummery, C. L., van den Eijnden-van Raaij, A. J. M. (1993) Type β transforming growth factors and activins in differentiating embryonal carcinoma cells, embryonic stem cells and early embryonic development. Int. J. Dev. Biol. 37:169-182.
4. Van Stekelenburg-Hamers, A. E. P., van Achterberg, T., Rebel, H., Flechon, J. E., Campbell, K. H. S., Weima, S, Mummery, C. L. (1995). Isolation and characterisation of permanent cell lines form the inner cell mass of bovine blastocysts. Mol. Reprod. Dev. 40:444-454.
5. Van Stekelenburg-Hamers A. E. P. thesis entitled "Developmental Potency in early bovine embryo's of October 5, 1994.

The invention claimed is:

1. A meat product produced by the process comprising:
culturing in vitro non-human animal cells selected from the group consisting of muscle cells, somite cells and stem cells, in a medium free of hazardous substances for humans, thereby producing a three dimensional animal muscle tissue,
processing the three dimensional animal muscle tissue to provide a finished meat product wherein deboning, removal of offal and/or tendon and/or gristle and/or fat is not required,
said finished meat product comprises solidified muscle cell tissue as the protein source, wherein the finished meat product is suitable for at least one of human and animal consumption, and wherein the finished meat product is in a form selected from the group consisting of sausage, spread, cooked puree, pureed baby food, biscuit, dried granules, tablet, capsule, powder, pickled meat product, smoked meat product, dried meat product and cooked meat product.

2. The meat product according to claim 1, free of growth hormones in amounts hazardous for consumption.

3. The meat product according to claim 1, further comprising nutritional additives selected from the group consisting of vitamins and minerals.

4. The meat product according to claim 1, wherein said meat product has a texture comparable to that of an in vivo derived meat product.

5. The meat product according to claim 1 in a unit form of at least 50 grams.

* * * * *